United States Patent
Kim et al.

(10) Patent No.: US 10,949,651 B2
(45) Date of Patent: Mar. 16, 2021

(54) ELECTROCARDIOGRAM-BASED FACE RECOGNITION SECURITY SYSTEM AND METHOD USING SMART WATCH

(71) Applicant: Dodotdo Co., Ltd, Seoul (KR)

(72) Inventors: In Gyeom Kim, San Diego, CA (US); So Yeong Sim, Seoul (KR)

(73) Assignee: DODOTDO CO., LTD, Seoul (KR)

( * ) Notice: Subject to any disclaimer, the term of this patent is extended or adjusted under 35 U.S.C. 154(b) by 202 days.

(21) Appl. No.: 16/233,668

(22) Filed: Dec. 27, 2018

(65) Prior Publication Data

US 2020/0202112 A1 Jun. 25, 2020

(30) Foreign Application Priority Data

Dec. 19, 2018 (KR) .................. 10-2018-0164955

(51) Int. Cl.
*G06K 9/00* (2006.01)
*G06F 21/32* (2013.01)
*A61B 5/1171* (2016.01)
*A61B 5/0402* (2006.01)

(52) U.S. Cl.
CPC ......... *G06K 9/00288* (2013.01); *G06F 21/32* (2013.01); *G06K 9/00248* (2013.01); *G06K 9/00302* (2013.01); *G06K 9/00885* (2013.01); *A61B 5/0402* (2013.01); *A61B 5/1176* (2013.01); *G06K 2009/00939* (2013.01)

(58) Field of Classification Search
CPC .......... G06K 9/00288; G06K 9/00885; G06K 9/00302; G06K 9/00248; G06K 2009/00939; G06F 21/32; A61B 5/1176; A61B 5/0402
See application file for complete search history.

(56) References Cited

U.S. PATENT DOCUMENTS

| | | | | |
|---|---|---|---|---|
| 2016/0162683 A1* | 6/2016 | Gibson | .................. | G06F 21/32 726/17 |
| 2016/0283703 A1* | 9/2016 | Allyn | ...................... | G06F 21/32 |
| 2017/0243225 A1* | 8/2017 | Kohli | ...................... | G07C 9/37 |
| 2019/0050238 A1* | 2/2019 | Lim | ........................ | G06F 16/00 |
| 2020/0042797 A1* | 2/2020 | Lee | .................... | G06K 9/00718 |

* cited by examiner

*Primary Examiner* — Siamak Harandi
(74) *Attorney, Agent, or Firm* — Hauptman Ham, LLP

(57) ABSTRACT

The present invention relates to an electrocardiogram-based face recognition security system and method using a smart watch, and more particularly, to a security system and a method for enhancing security by simultaneously performing biometric human identification based on an electrocardiogram and biometric human identification using face recognition for user identification in a portable PTT communication device such as smart watch.

8 Claims, 4 Drawing Sheets

ELECTROCARDIOGRAM-BASED FACE RECOGNITION SECURITY SYSTEM AND METHOD USING SMART WATCH

CROSS-REFERENCE TO RELATED APPLICATIONS

This application claims the benefit of Korean Patent Application No. 10-2018-0164955 filed with the Korean Intellectual Property Office on Dec. 19, 2018, the disclosures of which are incorporated herein by reference.

TECHNICAL FIELD

The present invention relates to an electrocardiogram-based face recognition security system and method using a smart watch, and more particularly, to a security system and a method for enhancing security by simultaneously performing biometric human identification based on an electrocardiogram and biometric human identification using face recognition for user identification in a portable PTT communication device such as smart watch.

BACKGROUND

In recent times, smart watches integrated with mobile phone functions are gathering attention. As mobile phones started adopting not only telephone networks but also Internet networks through which personal information, such as documents, finances and the like, are transmitted and received, the awareness on issues relating to mobile phone security is becoming prevalent.

The more complicated a user identification process becomes the more inconvenient mobile phone users feel. To address such issue, a biometric identification technology may be introduced to provide mobile phone security and user identification in a simple and convenient manner.

Biometrics identification refers to metrics for using personal information as identifiers based on physiological characteristics and behavioral characteristics. Examples include, but are not limited to fingerprint, retina, iris, face, hand, palm veins, voice, signature or DNA.

Fingerprint recognition is a technique of identifying a certain flow in a sweat gland protuberant in a finger, exhibiting efficiency in reliability and stability in performance. Such fingerprint recognition employs thinning, Fourier transform, wavelet transform, neural networks, or Fuzzy logic, and requires a process of de-noising and correction. Also used for fingerprint recognition are syntactic, statistical or rule-based schemes, neural networks, chain codes, or ridge-following. However, fingerprint recognition has disadvantages in that geometrical deformation may occur in fingerprints recognized based on the resolution of a fingerprint image, pixel distribution characteristics, a scanning scheme of a fingerprint input sensor and that ridge number extraction and the use of fingerprint recognition may be sensitive to the rotation and deformation of fingerprints and has low reproducibility.

Iris recognition refers to a technique of identifying individuals based on the form of an iris tissue. Although iris recognition has relatively low recognition error rate, it requires precise focal distance between an iris of a user and a scanner and has difficulty obtaining precise iris pattern when a user moves. When capturing an image of an iris, the color of an iris image may change, and thus, iris recognition may be made difficult in case of wearing a contact lens, such as a color lens.

Retina scanning recognizes the pattern of blood vessels within human retina. In retina scanning, the pattern of blood vessels may change depending on the presence of glasses or a contact lens, or blood alcohol concentration. Since it requires light irradiation from a scanner to eye during retina scanning, there is a risk of eye contamination due to direct contact of eye and the scanner.

Face recognition identifies individuals by capturing an image of a face in a non-contact manner, extracting a facial part from the captured image, and analyzing points for each characteristic of the face. Despite its simple process, it still faces challenges in commercialization thereof, because the shape of face may vary depending on an angle of face, facial expressions, or age and a matching rate is low.

Palm vein pattern identification identifies the pattern of palm veins using a contact-type infrared capturing device. Although it has an advantage in that vein patterns are non-duplicable, it is difficult to establish a database of vein patterns and requires rather expensive device.

In voice identification, there may be various obstructions, such as change in human voice in course of time or noise, and voice identification may have risks of voice fabrication/falsification.

SUMMARY

The present invention aims to provide a security system and method that enhances security by performing biometric human identification based on an electrocardiogram and biometric human identification through face recognition, and a PTT communication system using the security system.

However, the present invention should not be construed as being limited to the exemplary embodiments set forth herein, and rather, these exemplary embodiments are provided so that this disclosure will fully convey the scope of the invention to those skilled in the art.

In order to accomplish the above-mentioned purposes, some embodiments of the present invention provides an electrocardiogram-based face recognition security system comprising: a plurality of user terminals for enabling biometric human identification (HID) using electrocardiogram and face recognition and PTT communication, the user terminal is a smart watch providing a push-to-talk (PTT) communication service through interworking with a server including an electrocardiogram database and a face recognition database; and a server configured to receive electrocardiogram data, face recognition data and a PTT message from a first user terminal of the plurality of user terminals, transmit the electrocardiogram data to the electrocardiogram database, transmit the face recognition data to the face recognition database, transmit the PTT message to at least one a second user terminal of the plurality of user terminals which enters a corresponding PTT channel when the biometric HID is identified using the electrocardiogram database and the face recognition database.

The server may be provided in a hospital to store the electrocardiogram database and a user having the first user terminal may perform the PTT communication with a doctor in the hospital having the second user terminal.

Further, the user terminal comprises: a communication unit configured to modulate a frame applied to PTT communication to a PTT frequency signal to thereby transmit the modulated frame via an antenna, and demodulate the frequency signal received from the antenna to the frame; an input unit configured as a user input interface comprising a plurality of input keys, the input keys comprising a PTT button configured to support a PTT function in PTT communication; a biometric identification unit configured to perform a biometric HID method based on electrocardiogram and face recognition; an output unit configured to convert voice data input from a microphone into the frame to transmit the frame to the communication unit in a PTT transmission mode, and extracting voice data from the frame demodulated in the communication unit to output the voice data through a speaker in a PTT reception mode; a memory unit configured to store biometric HID program performed in a control unit and biometric HID data as well as input/out electrocardiogram data and face recognition data; and the control unit configured to control the communication unit, input unit, and the output unit to execute a PTT transmission mode when the PTT button is pushed and execute a PTT reception mode when the PTT button is released.

Further, a base form for entire waveform of each user is determined and the determination is performed by pulse forms grouped in a simple manner such as Low Below (LB), Medium Below (MB), High Below (HB), Low Up (LU), Medium Up (MU) and High Up (HU) and the pulse sequence for each user is aligned in the electrocardiogram database.

In order to accomplish the above-mentioned purposes, some embodiments of the present invention provides an electrocardiogram-based face recognition security method using a smart watch that includes biometric human identification (HID) device based on electrocardiogram and face recognition and provides a push-to-talk (PTT) communication service through interworking with a server including an electrocardiogram database and a face recognition database, the method comprises: receiving an input of face feature point data of a user; receiving an input of an electrocardiogram waveform of the user and removing the baseline noise from the received electrocardiogram waveform; determining a base form for each electrocardiogram waveform to determine a base form of the entire waveform for each user; classifying the waveform for the user by evaluating a change in the base form; extracting characteristics of the classified waveform to enable user identification; and generating identification information which allows user identification using a predetermined code set based on the extracted characteristics and input face feature point data to thereby perform user identification.

Further, the method comprises identifying pulse forms grouped in in a simple manner such as Low Below (LB), Medium Below (MB), High Below (HB), Low Up (LU), Medium Up (MU) and High Up (HU).

Further, the identifying further comprises: aligning a sequence of HID for each individual through a HID database server such that precision for HID and identification rate increase as a greater amount of heartbeat rate electrocardiogram data is collected.

According to some embodiments of the present invention, a biometric human identification based on an electrocardiogram and a biometric human identification through face recognition are combined to enhance security, and a PTT communication system using the security system is provided.

In addition, the method may interwork with a health care application in a smartphone to thereby manage user's health based on electrocardiogram data.

DESCRIPTION OF EMBODIMENTS

Figure 1:
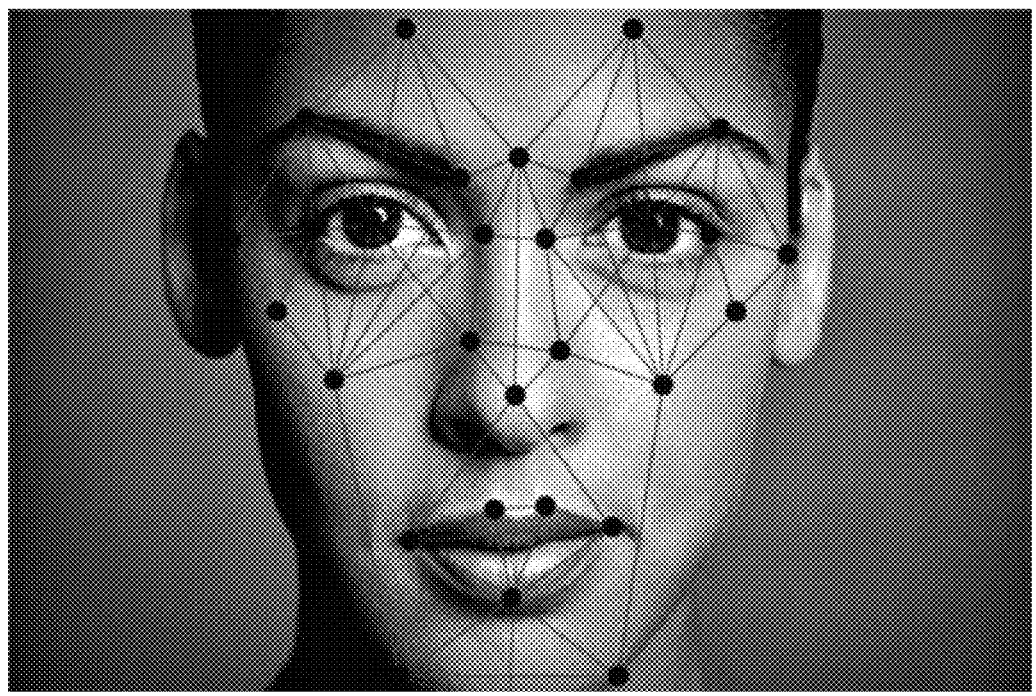
FIG. 1 is a diagram illustrating an exemplary feature point configuration in a face recognition method used in a security system in which security is improved by performing biometric human identification based on an electrocardiogram and biometric human identification through face recognition according to some embodiments of the present invention.

Advantages and features of the invention and methods for achieving them will be made clear from exemplary embodiments described below in detail with reference to the accompanying drawings. The invention may, however, be embodied in many different forms and should not be construed as being limited to the exemplary embodiments set forth herein. Rather, these exemplary embodiments are provided so that this disclosure will be thorough and complete, and will fully convey the scope of the invention to those skilled in the art. The invention is merely defined by the scope of the claims. Therefore, well-known constituent elements, operations and techniques are not described in detail in the exemplary embodiments in order to prevent the invention from being obscurely interpreted. Like reference numerals refer to like elements throughout the specification. The terminology used herein is for the purpose of describing embodiments only and is not intended to be limiting. As used herein, the singular forms "a," "an," and "the" are intended to include the plural forms, including "at least one," unless the content clearly indicates otherwise. "Or" means "and/or." As used herein, the term "and/or" includes any and all combinations of one or more of the associated listed items.

The terminology for a module used herein may be interpreted as including software, hardware or a combination thereof. For example, software may include machine language, firmware, embedded code, and application software. Examples of hardware may include a circuit, a processor, a computer, an integrated circuit, an integrated circuit core, a sensor, a micro-electro-mechanical system (MEMS), a manual device, or a combination thereof.

Exemplary embodiments will now be described more fully hereinafter with reference to the accompanying drawings. Hereinafter, a PTT smart watch system using a biometric human identification (HID) method based on electrocardiogram and face recognition will be referred to as a "PTT smart watch system."

FIG. 1 is a diagram illustrating an exemplary feature point configuration in a face recognition used in a security system in which security is improved by performing biometric human identification based on an electrocardiogram and biometric human identification through face recognition according to some embodiments of the present invention.

In the face recognition, a plurality of feature points formed on a face of a user are stored as feature point data. When the face of the user is identified through a sensor including a camera, the identified feature point data is compared with the stored feature point data to perform a biometric human identification.

However, there is a technical and economic limit in the face recognition since face recognition has a possibility of misidentification when using a user's photographic image, and a two-dimensional face recognition technique additionally requires a laser distance measuring device.

Further, face recognition identifies individuals by capturing an image of a face in a non-contact manner, extracting a facial part from the captured image, and analyzing points for each characteristic of the face. Despite its simple process, it still faces challenges in commercialization thereof, because the shape of face may vary depending on an angle of face, facial expressions, or age and a matching rate is low.

Therefore, in order to exclude the use of an additional expensive device for error correction in biometric human identification using the face recognition, the user's electrocardiogram bio-HID technique is combined to the face recognition to overcome the disadvantage of biometric human identification through face recognition only.

Figure 2:
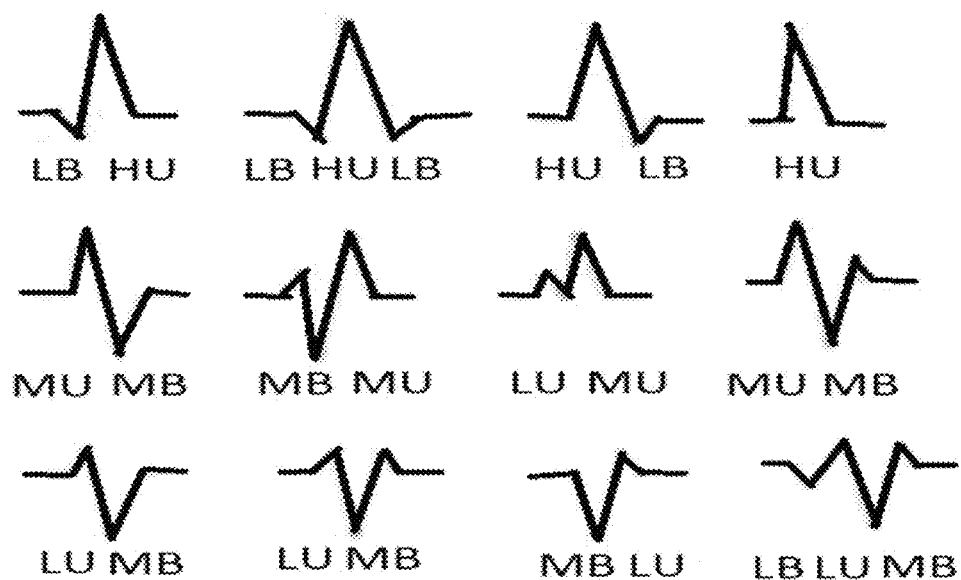
FIG. 2 is a diagram illustrating waveforms of an electrocardiogram human identification (HID) of an individual used in a security system in which security is improved by performing biometric human identification based on an electrocardiogram and biometric human identification through face recognition according to some embodiments of the present invention.

FIG. 2 is a diagram illustrating waveforms of an electrocardiogram human identification (HID) of an individual used in a security system in which security is improved by performing biometric human identification based on an electrocardiogram and biometric human identification through face recognition according to some embodiments of the present invention.

In the embodiment, a scheme of collecting biometric electrocardiogram data conducts HID by logging-into an account by identifying pulse forms grouped in a simple manner such as low below (LB), medium below (MB), high below (HB), low up (LU), medium up (MU), or high up (HU), and aligns a sequence of HID for each individual through the HID database server (200) such that precision for HID and identification rate increase as a greater amount of heartbeat rate electrocardiogram data is collected. The sequence of HID for each individual is a series of code connected by a combination of LB, MB, HB, LU, MU, or HU as shown in FIG. 2.

The precision for electrocardiogram-based HID may increase as a greater amount of heartbeat rate electrocardiogram data is collected. Since a main user is rapidly identified and a non-user is not rapidly identified, a greater amount of data does not need to be collected for the main user, thus increasing an identification rate. In addition to the use of electrocardiogram data for HID, the electrocardiogram data stored in a server and interworking with a health care application of the user terminals (100a, 100b) may be also used for managing user's health.

Figure 3:
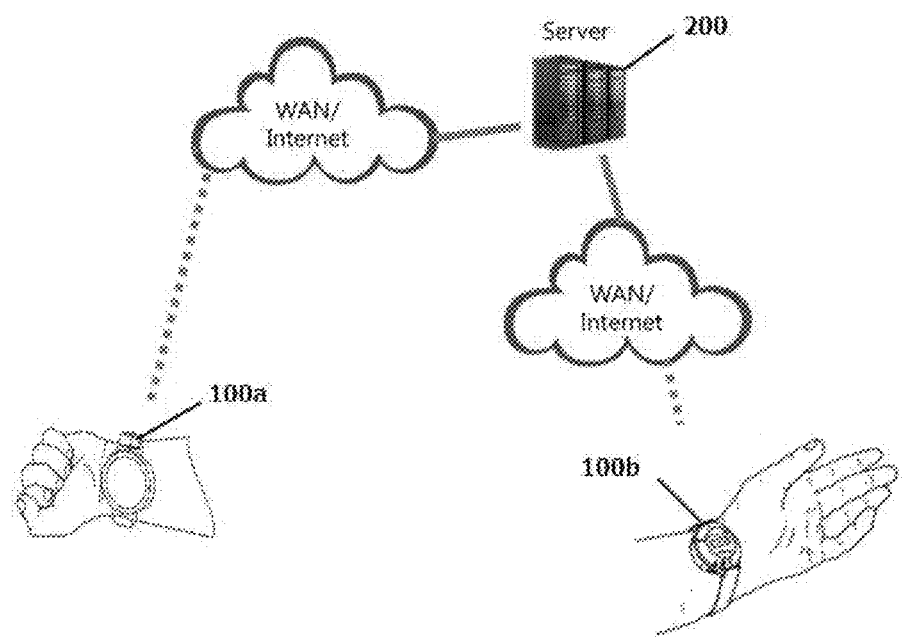
FIG. 3 is a schematic diagram of a smart watch PPT system to which a security system with enhanced security is applied in parallel with a biometric human identification based on an electrocardiogram and a biometric human identification based on face recognition according to some embodiments of the present invention.

FIG. 3 is a schematic diagram of a smart watch PPT system to which a security system with enhanced security is applied in parallel with a biometric human identification based on an electrocardiogram and a biometric human identification based on face recognition according to some embodiments of the present invention.

Referring to FIG. 3, a biometric identification smart watch system provides a PTT service through interworking with a server including an electrocardiogram database and face recognition database. The biometric identification smart watch system comprises: a plurality of user terminals (100a, 100b) enabling biometric identification and PTT communication; and a server (200) configured to receive electrocardiogram data, facial feature point data and a PTT message from a first user terminal (100a) of the plurality of user terminals, transmit the electrocardiogram data to an electrocardiogram database, transmit the facial feature point data to a face recognition database, and transmit the PTT message to at least one second user terminal (100b) of the plurality of user terminals which enters a corresponding PTT channel when biometric HID is identified from the electrocardiogram database and the face recognition database.

The first user terminal (100a) extracts facial feature point data and measures an electrocardiogram waveform of a user. Then, the first user terminal (100a) compares the extracted facial feature point data with existing facial recognition data stored in the facial recognition database, compares a waveform of the electrocardiogram of the user with an existing electrocardiogram waveform stored in the electrocardiogram database, identifies the user, and transmits data on the identification of the user to the server (200). The server (200) stores data on the electrocardiogram and face feature points of the user and transmits a signal to enable PTT communication with the second user terminal (100b). The second user terminal (100b) receives a signal of the first user terminal (100a) transmitted from the server (200) and performs PTT communication.

The user terminals (100a, 100b) are provided for efficient mobile communication of a wearable smart watch. However, such small-sized wearable smart watches require an identification technique for more rapid PTT communication while ensuring security. Since screens for wearable smart watches are small, a user identification technique for wearable smart watches is significant.

In some embodiments, the user terminals (100a, 100b) transmit/receive information with the server (200) via the wireless access network (WAN) or the Internet, and the user terminals (100a, 100b) transmit/receive information with each other via a mobile communication network.

In some embodiments, an electrocardiogram data server may be provided in a hospital so that a doctor may use electrocardiogram data of a user to diagnose the user's health, and the user may have a consultation with the doctor as to the user's health in a convenient manner using PTT communication. For example, in emergency, the user may remotely contact the doctor conveniently using PTT communication.

The biometric HID method based on electrocardiogram and face recognition may be implemented in a computer system or recorded in a recording medium. The computer system may include at least one processor, a memory, a user input device, a data communication bus, a user output device and a storage. These elements each perform data communication through the data communication bus.

The computer system may further include a network interface coupled in a network. The processor may be a central processing unit (CPU) or a semiconductor device that processes a command stored in a memory and/or a storage.

The memory may further include a volatile or non-volatile storing medium in various forms. For example, the memory may include a read only memory (ROM) and a random access memory (RAM).

The biometric HID method based on electrocardiogram and face recognition may be implemented as a computer-readable code in a computer-readable recording medium. The computer-readable recording medium may include all types of recording medium storing data that is interpretable by a computer system. Examples of the computer-readable recording medium may include a ROM, a RAM, a magnetic tape, a magnetic disk, a flash memory, or an optical data storage. In addition, the computer-readable recording medium may be distributed in a computer system connected by a computer communication network, stored as a code readable in a distribution manner and performed.

Figure 4:
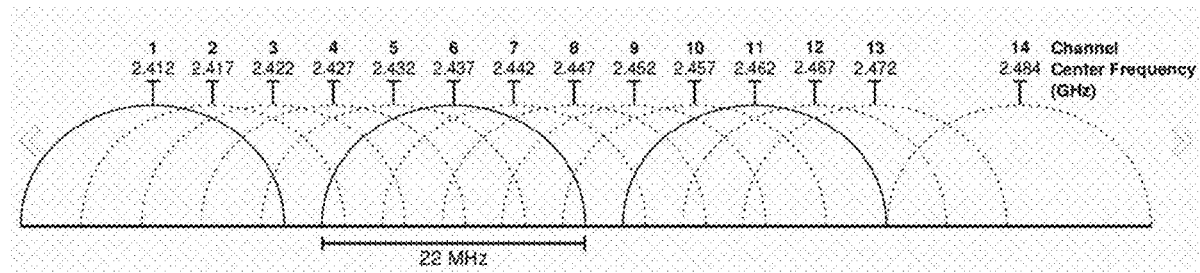
FIG. 4 is a schematic diagram of a frequency range used in a smart watch PTT system to which a security system with enhanced security is applied in parallel with a biometric human identification based on an electrocardiogram and a biometric human identification based on face recognition according to some embodiments of the present invention.

FIG. 4 is a schematic diagram of a frequency range used in a smart watch PTT system to which a security system with enhanced security is applied in parallel with a biometric human identification based on an electrocardiogram and a biometric human identification based on face recognition according to some embodiments of the present invention.

Referring to FIG. 4, a PTT smart watch system in 802.11b, 802.11g, and 802.11n uses a spectrum in a range from 2.400 GHz to 2.500 GHz and an industry-science-medical (ISM) band uses a range from 4.915 to 5.825 GHz, which is a higher frequency range. Although 2.4 GHz and 5 GHz bands are commonly used, the respective spectra are divided into channels having a center frequency and a bandwidth, and into radio and TV broadcast bands in an analog scheme. A 2.4 GHz band, which is divided into 14 channels with an interval of 5 MHz, starts from channel 1 and has a center frequency at 2.412 GHz. Communication in such bandwidths is used to increase mobility of a PTT smart watch and enable low power consumption.

Figure 5:
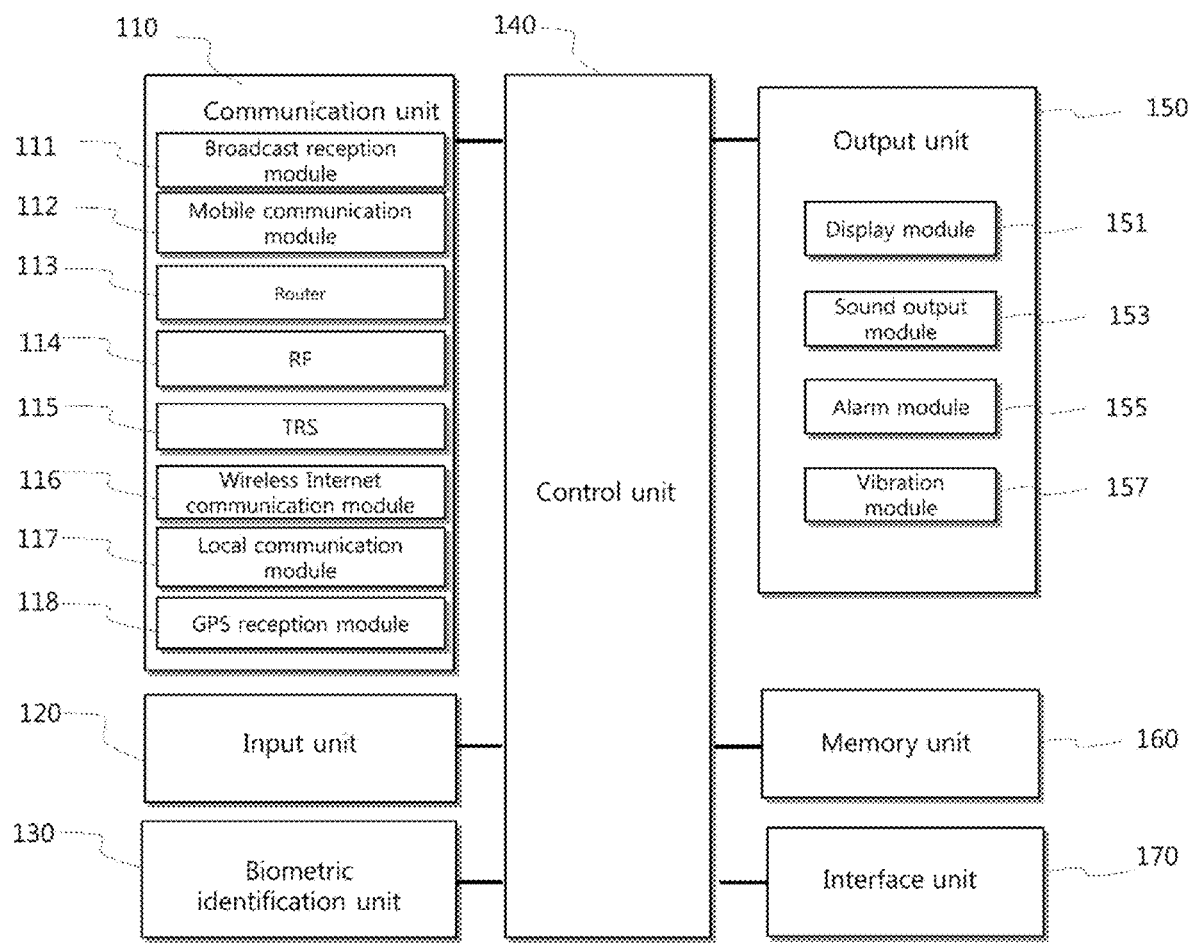
FIG. 5 is a block diagram of a smart watch PTT device to which a security system with enhanced security is applied in parallel with a biometric human identification based on an electrocardiogram and a biometric human identification through face recognition according to some embodiments of the present invention.

FIG. 5 is a block diagram of a smart watch PTT device to which a security system with enhanced security is applied in parallel with a biometric human identification based on an electrocardiogram and a biometric human identification through face recognition according to some embodiments of the present invention.

Referring to FIG. 5, PTT user terminals (100a, 100b) using a biometric HID method based on electrocardiogram and face recognition provides a PTT service through inter-working with a server (200) including an electrocardiogram database and a face recognition database.

The user terminals (100a, 100b) may include: a communication unit (110) configured to modulate a frame applied to PTT communication to a PTT frequency signal to thereby transmit the modulated frame via an antenna, and demodulate the frequency signal received from the antenna to the frame; an input unit (120) configured as a user input interface comprising a plurality of input keys, the input keys comprising a PTT button configured to support a PTT function in PTT communication; a biometric identification unit (130) configured to perform a biometric HID method based on electrocardiogram and face recognition; an output unit (150) configured to convert voice data input from a microphone into the frame and transmit the frame to the communication unit (110) in a PTT transmission mode, and extract voice data from the frame demodulated in the communication unit (110) to output the voice data through a speaker in a PTT reception mode; a memory unit (160) configured to store biometric HID program for electrocardiogram and face recognition performed in a control unit (140) and store input/output biometric HID data including electrocardiogram data and face recognition data; an interface unit (170) configured to transmit/receive signals among the respective units; and a the control unit (140) configured to control the communication unit (110), input unit (120), and the output unit (150) so as to execute a PTT transmission mode when the PTT button is pushed and execute a PTT reception mode when the PTT button is released during PTT communication.

In FIG. 5, the PTT user terminals (100a, 100b) may include the communication unit (110), the input unit (120), the biometric identification unit (130), the control unit (140), the output unit (150), the memory unit (160), the interface unit (170), and a power supply (not shown).

The communication unit (110) may include at least one module that enables wireless communication between the user terminal (100a) and the user terminal (100b). The communication unit (110) may include at least one of a broadcast reception module (111), a mobile communication module (112), a wireless Internet communication module (116), a local communication module (117) and a global positioning system (GPS) reception module (118).

The broadcast reception module (111) may receive a broadcast signal and broadcast-related information from an external broadcast management server through a broadcast channel.

The mobile communication module (112) may include a router (113), a trunk radio system (TRS) (115), an RF (114), and transmit/receive wireless signals with a base station, a repeater, a femtocell, or a radio remote head (RRH) via a wireless interface of mobile communication network.

The router (113) is a device for sharing two different frequency signals via a single route. In a case where the RF (114) and the TRS (115) have separate antennas, there is no need for such router (113).

The RF (114) performs wireless communications according to a wireless communication protocol such as wideband code division multiple access (WCDMA). The RF (114) may include an RF transmitter that up-converts and amplifies a frequency of a signal transmitted therefrom and an RF receiver that low-noise amplifies a signal received thereto and down-converts the frequency of the signal.

The TRS (115) performs wireless communications according to a communication protocol of a TRS (Trunk Radio System) using a trunked radio system network. The TRS uses a very high frequency (VHF) or an ultra high frequency (UHF) on a charged basis and a radio frequency (RF) distance of the TRS is formed within a range of 10 Km to 20 Km.

The wireless Internet communication module (116) is a transception module for wireless Internet connection. The wireless Internet communication module (116) may be embedded in a wearable device (100) or externally provided through a predetermined interface terminal.

The local communication module (117) is a module for local communication such as NFC (Near Field Communication) and Bluetooth.

The GPS reception module (118) is a module configured to verify or obtain location information of the PTT smart watch system (100) using a signal received from satellites.

The input unit (120) is configured to operate as a number key for inputting number and character data and a function key for setting various functions. Examples of the function key may include speaker ON/OFF buttons, a volume control button, and a PTT button.

The biometric identification unit (130) conducts biometric HID method based on electrocardiogram and face recognition. The biometric HID method based on electrocardiogram and face recognition conducted in the biometric identification unit (130) may be conducted in the smart watches (100a, 100b) or the biometric HID method can be conducted by a corresponding biometric identification unit (not shown) in the server (200). The biometric identification unit (130) may use electrocardiogram, fingerprint, retina, iris, face, hand, palm veins, voice, signature, or DNA as biometric identifiers.

The control unit (140) is configured to control the communication unit (110), the input unit (120), the biometric identification unit (130), the output unit (150), the memory unit (160), and the interface unit (170) so as to execute a PTT transmission mode when the PTT button is pushed and execute a PTT reception mode when the PTT button is released during a PTT communication.

The output unit (150), for example, a liquid crystal display (LCD) device, displays an image signal output from an image-processing unit on a screen and displays user data output from the control unit (140). The output unit (150) may comprise a display module (151) or a sound output module (153) for generating visual, auditory or haptic outputs.

The display module (151) is configured to display data processed in the PTT smart watch system.

The sound output module (153) is configured to output a predetermined sound alarm signal for notifying a user when a voice message from another user is received through a PTT application from the wireless communication unit (110). The sound output module (153) may output audio data stored in the memory unit (160).

The alarm module (155) is configured to output a signal for notifying an occurrence of an event in the PTT smart watch system.

The vibration module (157) is configured to generate various haptic effects for a user to sense.

The memory unit (160) is configured to store biometric HID program performed in the control unit (140), biometric HID data and input/output electrocardiogram data and face recognition data.

The interface unit (170) enables signal transmission among the respective units.

The power supply unit (not shown) is configured as a battery for supplying power to the respective functional units. For a maximum battery lifetime, power consumption needs to be reduced to the minimum. To this end, a mobile phone with a radio communication function may operate in a walkie-talkie mode, which is a family radio communication function and the power consumption may be significantly reduced through a sleep mode and a wake-up mode.

Figure 6:
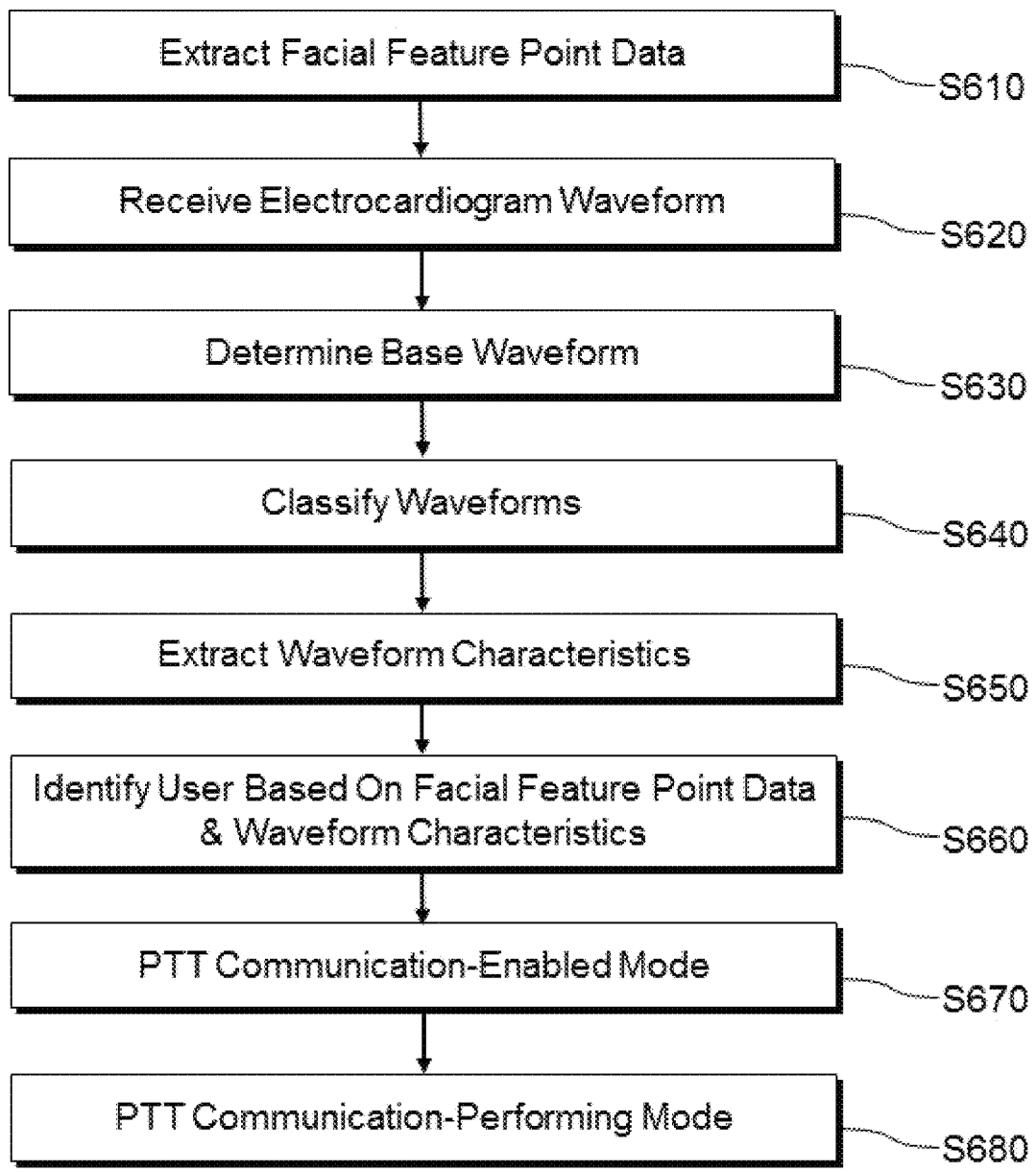
FIG. 6 is a flowchart of a smart watch PTT method using a security system that enhances security by performing biometric human identification based on an electrocardiogram and biometric human identification based on face recognition according to some embodiments of the present invention.

FIG. 6 is a flowchart of a smart watch PTT method using a security system that enhances security by performing biometric human identification based on an electrocardiogram and biometric human identification based on face recognition according to some embodiments of the present invention.

Referring FIG. 6, a biometric HID method based on electrocardiogram and face recognition is performed at a PTT smart watch provided with a biometric HID device based on electrocardiogram and face recognition and interworked with a PTT server to provide a PTT service. The biometric HID method may include: producing facial feature point data by extracting facial feature points from a user (S610); receiving an input of an electrocardiogram waveform of the user and removing the baseline noise of the electrocardiogram waveform (S620); determining a base form for each waveform to determine a base form of the entire waveform for each user (S630); evaluating a change in the base form for each waveform to classify a corresponding waveform (S640); extracting characteristics of the corresponding waveform based on the extracted waveform so as to enable user identification (S650); generating identification information which allows user identification using a predetermined code set based on the extracted characteristics and the facial feature points to thereby perform user identification (S660); performing a PTT communication-enabled mode when the user is identified (S670); and performing PTT transmission and PTT reception in a PTT communication performing mode (S680).

In operation S620, the first user terminal (100a) inputs an electrocardiogram waveform of a corresponding user. The first user terminal (100a) removes baseline noise of the electrocardiogram waveform. Otherwise, the process of removing baseline noise of the electrocardiogram waveform may be carried out in the server (200).

In operation S630, the first user terminal (100a) determines a base form of each waveform to determine a base form of the entire waveform for the user. The process of determining of a base form of entire waveform for the user may be carried out in the server (200).

In operation S640, the first user terminal (100a) evaluates a change in the base form for each waveform and classifies them. The evaluating of a change in the base form for each waveform to classify waveforms may be carried out in the server (200).

In operation S650, the first user terminal (100a) extracts characteristics of the classified waveform for user identification. The process of extracting of characteristics from the classified waveform may be carried out in the server (200).

In operation S660, the first user terminal (100a) generates identification information which allows user identification using a predetermined code set based on the extracted characteristics in the waveform and face recognition data. The generating of identification information which allows user identification using a predetermined code set based on the extracted characteristics and face recognition data may be carried out in the server (200).

In operation S670, the first user terminal (100a) performs a PTT communication-enabled mode when the user is identified.

In operation S680, when a PTT transmission mode is executed by the PTT button is pushed in the first user terminal (100a), a signal is transmitted to the second user terminal (100b) to thereby execute a PTT reception mode in the second user terminal (100b), and when the PTT button is released in the first user terminal (100a), the PTT reception mode is executed in the first user terminal (100a).

While the present invention has been described in connection with what is presently considered to be the most practical and preferred embodiments, it is to be understood that the invention is not limited to the disclosed embodiments, but, on the contrary, it will be understood by those skilled in the art that various changes in form and details may be made therein without departing from the spirit and scope of the invention as defined by the appended claims. It is therefore to be understood that the above-described embodiments are illustrative and non-restrictive in every respect. For example, each component described as a single entity may be distributed and implemented, and components described as being distributed may also be implemented in a combined form. Accordingly, the true scope of the present invention should be determined only by the appended claims.

The invention claimed is:

1. An electrocardiogram-based face recognition security system comprising:
   a plurality of user terminals for enabling biometric human identification (HID) using electrocardiogram and face recognition and push-to-talk (PTT) communication, wherein a first user terminal, among the plurality of user terminals, is a smart watch providing a PTT communication service through interworking with a server including an electrocardiogram database and a face recognition database; and
   a server configured to receive electrocardiogram data, face recognition data and a PTT message from the first user terminal of the plurality of user terminals, transmit the electrocardiogram data to the electrocardiogram database, transmit the face recognition data to the face recognition database, transmit the PTT message to a second user terminal, among the plurality of user terminals, which enters a corresponding PTT channel when the biometric HID is identified using the electrocardiogram database and the face recognition database.

2. The system of claim 1, wherein the server is provided in a hospital to store the electrocardiogram database and a user having the first user terminal may perform the PTT communication with a doctor in the hospital having the second user terminal.

3. The system of claim 1, wherein the first user terminal comprises:
   a communication unit configured to modulate a frame applied to PTT communication to a PTT frequency signal to thereby transmit the modulated frame via an antenna, and demodulate the frequency signal received from the antenna to the frame;
   an input unit configured as a user input interface comprising a plurality of input keys, the input keys comprising a PTT button configured to support a PTT function in PTT communication;
   a biometric identification unit configured to perform a biometric HID method based on electrocardiogram and face recognition;
   an output unit configured to convert voice data input from a microphone into the frame to transmit the frame to the communication unit in a PTT transmission mode, and extracting voice data from the frame demodulated in the communication unit to output the voice data through a speaker in a PTT reception mode;
   a memory unit configured to store biometric HID program performed in a control unit and biometric HID data as well as input/out electrocardiogram data and face recognition data; and
   the control unit configured to control the communication unit, input unit, and the output unit to execute a PTT transmission mode when the PTT button is pushed and execute a PTT reception mode when the PTT button is released.

4. The system of claim 3, wherein
   a base form for entire waveform of each user is determined and the determination is performed by pulse forms grouped in a simple manner such as Low Below (LB), Medium Below (MB), High Below (HB), Low Up (LU), Medium Up (MU) and High Up (HU).

5. The system of claim 4, wherein
   the pulse sequence for each user is aligned in the electrocardiogram database.

6. An electrocardiogram-based face recognition security method using a smart watch that includes biometric human identification (HID) device based on electrocardiogram and face recognition and provides a push-to-talk (PTT) communication service through interworking with a server including an electrocardiogram database and a face recognition database, the method comprises:
   receiving an input of face feature point data of a user;
   receiving an input of an electrocardiogram waveform of the user and removing the baseline noise from the received electrocardiogram waveform;
   determining a base form for the received electrocardiogram waveform to determine a base form of the entire waveform for the user;
   classifying the waveform for the user by evaluating a change in the base form;
   extracting characteristics of the classified waveform to enable user identification; and
   generating identification information which allows the user identification using a predetermined code set based on the extracted characteristics and input face feature point data to thereby perform the user identification.

7. The method of claim 6, wherein the determining further comprises:
   identifying pulse forms grouped in in a simple manner such as Low Below (LB), Medium Below (MB), High Below (HB), Low Up (LU), Medium Up (MU) and High Up (HU).

8. The method of claim 7, wherein the identifying further comprises:
   aligning a sequence of HID for each individual through a HID database server such that precision for HID and identification rate increase as a greater amount of heartbeat rate electrocardiogram data is collected.

* * * * *